United States Patent [19]

Hata

[11] 3,949,069

[45] Apr. 6, 1976

[54] NITROGEN-CONTAINING CARBOHYDRATE

[75] Inventor: Shun-ichi Hata, Yokohama, Japan

[73] Assignee: Chugai Seiyaku Kabushiki Kaisha, Tokyo, Japan

[22] Filed: Mar. 22, 1974

[21] Appl. No.: 453,988

[30] Foreign Application Priority Data

Mar. 26, 1973 Japan.............................. 48-33554

[52] U.S. Cl.................................. 424/95; 424/106

[51] Int. Cl.² .................. A61K 35/12; A61K 35/56; A61K 35/40

[58] Field of Search...................... 424/95, 106, 116

Primary Examiner—Jerome D. Goldberg
Attorney, Agent, or Firm—Browdy and Neimark

[57] ABSTRACT

A novel nitrogen-containing carbohydrate can be obtained from a proliferating tissue. The carbohydrate has an activity against transplanted Krebs-2 and Sarcoma-180 tumors in mice and also may be used as a diagnostic ingredient for the detection of such tumors.

1 Claim, 5 Drawing Figures

NITROGEN-CONTAINING CARBOHYDRATE

BACKGROUND OF THE INVENTION

This invention relates to a novel nitrogen-containing carbohydrate having activity against transplanted Krebs-2 and Sarcoma-180 tumors in mice.

It has been experimentally observed that a proliferating tissue, e.g. embryonal liver tissue, inhibits growth of tumor when they are injected in an experimental tumor-bearing animal, and the phenomenon has been discussed in relation to common antigenicity on the cell membranes of embryonal liver cells and tumor cells. That is to say, it has been recognized that common anti-bodies are produced in a body of the tumor-bearing animal in a higher concentration than usual by the injection of embryonal liver cells and, as a result, growth of tumor is inhibited immunologically, since tumor cells and embryonal liver cells are similar to each other in the point of their high proliferation speed and these two kinds of cells have several kinds of common antigens on their cell membranes. Thus, it is known that a proliferating tissue has anti-tumoral activity, but it has been thought that its anti-tumoral activity is due to its immunological mechanism and has not been thought that it is due to direct effect of a special substance in the proliferating tissue.

The present inventor found that proliferating tissues, e.g. tumor tissue, embryonal tissue and germ tissue, have a characteristic nitrogen-containing carbohydrate commonly on their cell membranes and has completed this invention through further investigation of cell fractions of these tissues.

BRIEF SUMMARY OF THE INVENTION

This invention relates to a novel nitrogen-containing carbohydrate having activity against transplanted Krebs-2 and Sarcoma-180 tumors in mice.

More particularly, the nitrogen-containing carbohydrate of this invention shows anti-tumoral activity in such experimental tumors of mice in a dose of 10 – 20 mg/head/day, i.p., for several days, and this substance may be utilized as a diagnostic ingredient for early detection of such tumor, since the substance has a stimulating activity of blastgenesis in lymphocytes of such tumor-bearing animals.

The novel nitrogen-containing carbohydrate of this invention can be obtained by the following steps:

a. extracting a homogenized proliferating tissue with about 2.5 to 10 times its volume of distilled water or a physiologically acceptable salt solution to obtain an extract solution, b. removing debris and contaminated protein by heating and centrifugation, c. adding twice the volume of an organic solvent, e.g. ethanol, acetone, pyridine, to the extract solution and collecting the resulting precipitates, d. dissolving the obtained precipitates in about 30 times volume of distilled water or a physiologically acceptable salts solution and filtering the solution through ultrafiltration membrane to collect membrane impermeable fractions, e. dissolving again the membrane impermeable fractions in a small amount of distilled water or a physiologically acceptable salts solution and contacting the solution with a bufferized anion exchange resin to remove proteineous impurities, f. carrying out column chromatography using a dextran gel having a molecular weight fractionation range of more than 10,000 and phosphate buffer solution as an effluence liquid to obtain an eluate, g. dialyzing the eluate against running water in a cellophane tube, concentrating the dialysate, and distilling the concentrate in vacuo with about 2 times its volume of an organic solvent, e.g. ethanol, acetone, or lyophilizing the concentrate, dissolved in distilled water.

As a proliferating tissue, a tumor tissue, an embryonal tissue and a germ tissue may be used. The tumor tissue may be, for example, Krebs-2, Sarcoma-180 and original hepatoma of human being, but any other kind of tumor tissue may also be used. As the embryonal tissue, the liver may be most advantageously used in view of its large size, and as the germ tissue ovary is used in case of animals and the germ tissue of kidney beans, Jack beans and the like may be used in case of plant.

A preferred method for preparing the nitrogen-containing carbohydrate is as follows:

First of all, the proliferating tissue is washed well with a physiological saline solution and homogenized with about 2.5 to 10 times its volume of neutral or alkaline buffer solution, preferably phosphate buffer solution, pH 6.0 – 7.0. The thus obtained homogenate is centrifuged at 12,000 $\times g$ for about 10 minutes and the supernatant is heated at 100°C. for about 2 hours on a water bath. The resulted precipitate is removed. The supernatant is concentrated to 1/10 its volume, and precipitates are obtained with the addition of about 2 times the volume of an organic solvent, e.g. ethanol, acetone, pyridine, etc. The precipitates are dissolved in about 30 times their volume of distilled water and the solution is filtered through ultrafiltration membrane to obtain an active fraction on the membrane. This active fraction is dissolved in a small amount of distilled water and the solution is passed through an anion exchange resin column bufferized with ammonium formate at a pH 6.0 – 7.0, whereby the proteineous impurities adsorbs on the resin and the active cell fraction is eluted from the column.

The eluate is passed through a dextran gel column with dextran gel having a molecular weight fractionation range of more than 10,000 and the active substance is eluted with a phosphate buffer solution, pH 6.0 – 7.0. The active fraction is, then, dialyzed against running water in a cellophane tube to remove inorganic salts, and the dialysate is condensed and distilled in vacuo with about 2 times volume of an organic solvent, e.g. ethanol, acetone, or dissolved in a small amount of distilled water after condensation and lyophilized, to give a powdery product.

Physicochemical properties of the nitrogen-containing carbohydrate are as follows:

1. Appearance:
   Colorless, powdery
2. Solubility:
   Easily soluble in water. Hardly soluble in organic solvents such as methanol, ethanol, acetone and ether.
3. Melting point:
   230°C (decomposed).
4. Ultraviolet absorption spectrum:
   No characteristic absorption.
5. Infrared absorption spectrum:

The spectrum is shown in FIG. 5 (KBr disc method).
Absorptions: 3400 – 3300, 1650, 1550, 1400, 1070 cm$^{-1}$ 6. Elemental analysis:
C; 34.4%, H; 9.7%, N; 8.2%, O; 38.2%

7. Molecular weight:
Ranges between 10,000 and 30,000 by the method using ultrafiltration membranes Diaflo, PM-30, PM-10, UM-2 and UM-05 and an ultrafiltration apparatus (available from Amicon Corp.).

8. Color reaction:

| | |
|---|---|
| Elson-Morgan's reaction | Positive |
| Molish reaction | Positive |
| Anthron reaction | Positive |
| Diphenylamine-HCl reaction | Positive |
| Ninhydrin reaction | Negative |
| Sialic acid reaction with Ehrlich's reagent | Negative |

9. Specific rotatory power:
$[\alpha]_D^{20} = -12°$

DETAILED DESCRIPTION OF THE INVENTION

The present invention is further illustrated by the following experiments and examples but these are given for exemplifying the specific embodiments only and are not to be construed as limiting the scope of the invention.

EXPERIMENTAL EXAMPLE 1

Swiss strain mice weighing 18 – 23 g, bred with a commercially available solid diet and water, were used.

The mice were divided into four groups of ten each. Each mouse was injected subcutaneously with 0.1 ml of ascitic fluid containing 25 × 10$^7$ cells of Sarcoma-180 or Krebs-2, in the area of the right shoulder, and from the second day 10 – 20 mg of the nitrogen-containing carbohydrate, obtained from original hepatoma of human being in the same manner as in Example 1, was injected intraperitoneally every day for seven days with 0.1 ml of phsiological saline solution.

On the tenth day after inoculation of tumor, the animals were sacrificed and the proliferated tumor tissue was isolated to determine the weights of tumor. The following results were obtained. A physiological saline solution was used as a control.

Table 1

| | Krebs-2 | | | Sarcoma-180 | |
|---|---|---|---|---|---|
| Animal No. | Untreated group mg | Treated group mg | Animal No. | Untreated group mg | Treated group mg |
| 1 | 1500 | 530 | 1 | 970 | 320 |
| 2 | 1240 | 725 | 2 | 1120 | 450 |
| 3 | 1310 | 430 | 3 | 1050 | 465 |
| 4 | 1175 | 625 | 4 | 950 | 380 |
| 5 | 960 | 500 | 5 | 1010 | 380 |
| 6 | 1450 | 450 | 6 | 1200 | 420 |
| 7 | 1390 | 615 | 7 | 980 | 350 |
| 8 | 1580 | 570 | 8 | 960 | 390 |
| 9 | 1240 | 490 | 9 | 1050 | 440 |
| 10 | 1610 | 320 | 10 | 1090 | 480 |
| Average | 1340 | 525 | Average | 1038 | 407 |

Table 1-continued

These results show that the nitrogen-containing carbohydrate obtained from original hepatoma of human being has an inhibitory effect of 40% on the experimental tumor of mice.

EXPERIMENTAL EXAMPLE 2

Swiss strain mice weighing 18 – 23 g, bred with a commercially available solid diet and water, were used.

The mice were divided into three groups of 10 each. Each mouse was injected subcutaneously with 0.1 ml of ascitic fluid containing 25 × 10$^7$ cells of Krebs-2, in the area of the right shoulder, and from the second day 10 or 20 mg of the nitrogen-containing carbohydrate, obtained from the tumor tissue of Krebs-2 in the same manner as in Example 1, was injected intraperitoneally every day for seven days with 0.1 ml of physiological saline solution.

Figure 1:
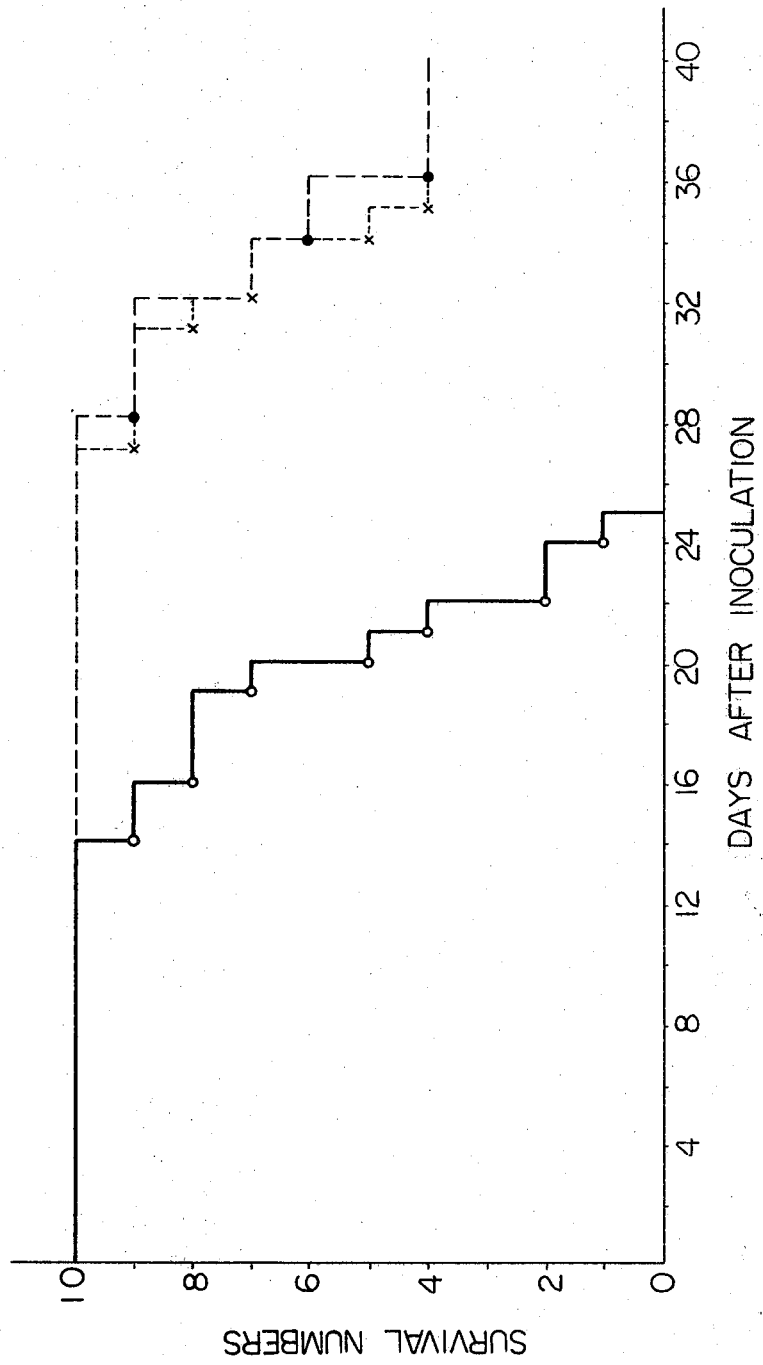
FIGS. 1 – 4 show anti-tumoral activity of the nitrogen-containing carbohydrate in transplanted Krebs-2 tumor-bearing mice (the effect of life-prolongation). In each of FIGS. 1 – 4, a solid line shows the result for a control group, a broken line shows the result for a group treated with 20 mg of the carbohydrate per day and a series of dots shows the result for a group treated with 10 mg of the carbohydrate per day.

Survival numbers were observed over 40 days after tumor inoculation. Results are shown in FIG. 1. All of the mice in the control group died before the 25th day after inoculation of tumor, while about 40 percent of the mice in the treated group were alive, even on the 40th day after inoculation of tumor.

EXPERIMENTAL EXAMPLE 3

Swiss strain mice weighing 18 – 23 g, bred with a commercially available solid diet and water, were used.

In the same manner as in Experimental Example 2, the nitrogen-containing carbohydrates were administered to mice; the carbohydrate obtained from Sarcoma-180 to the mice inoculated with Sarcoma-180, the carbohydrate obtained from embryonal liver tissue to the mice inoculated with Krebs-2 and the carbohydrate obtained from the ovary of a rat to the mice inoculated with Sarcoma-180.

Figure 2:
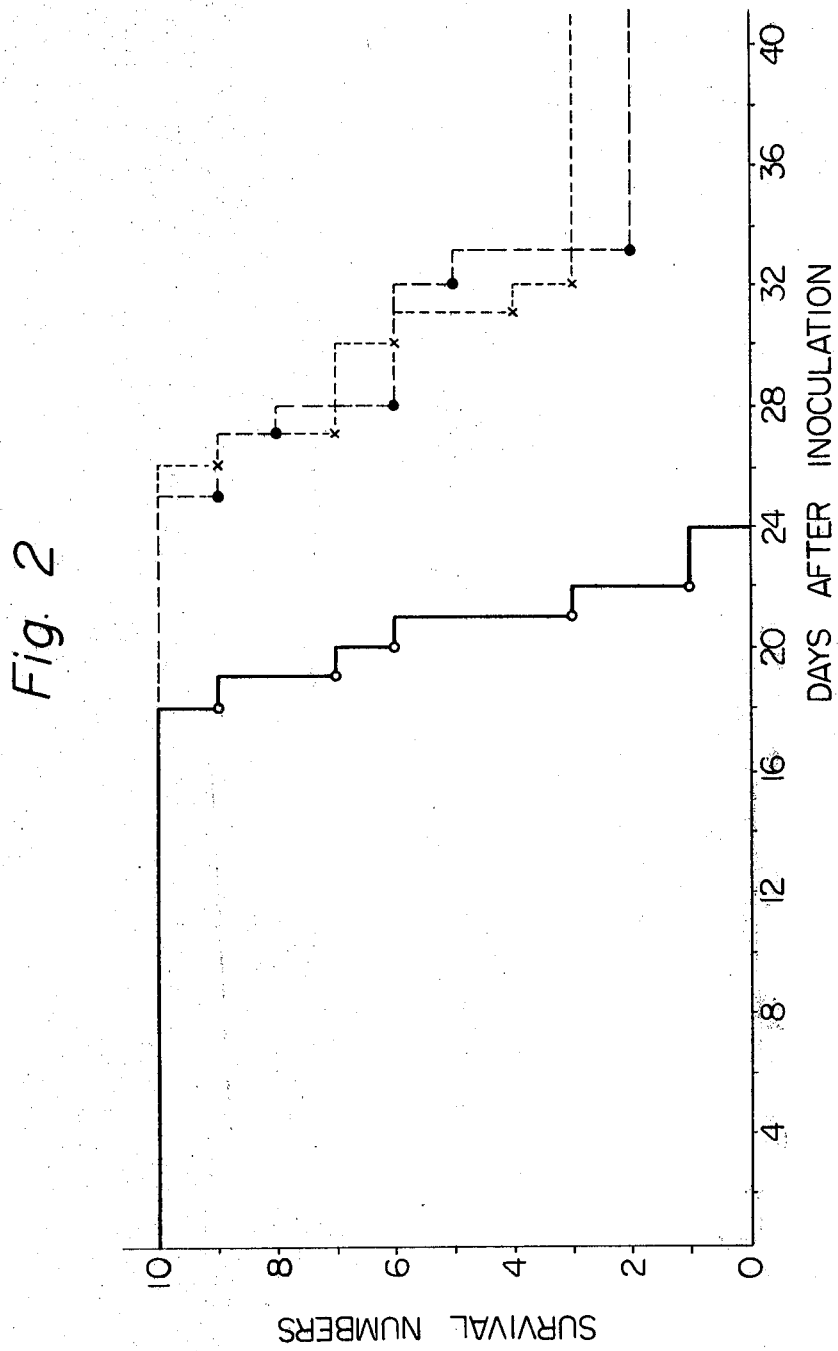
Figure 3:
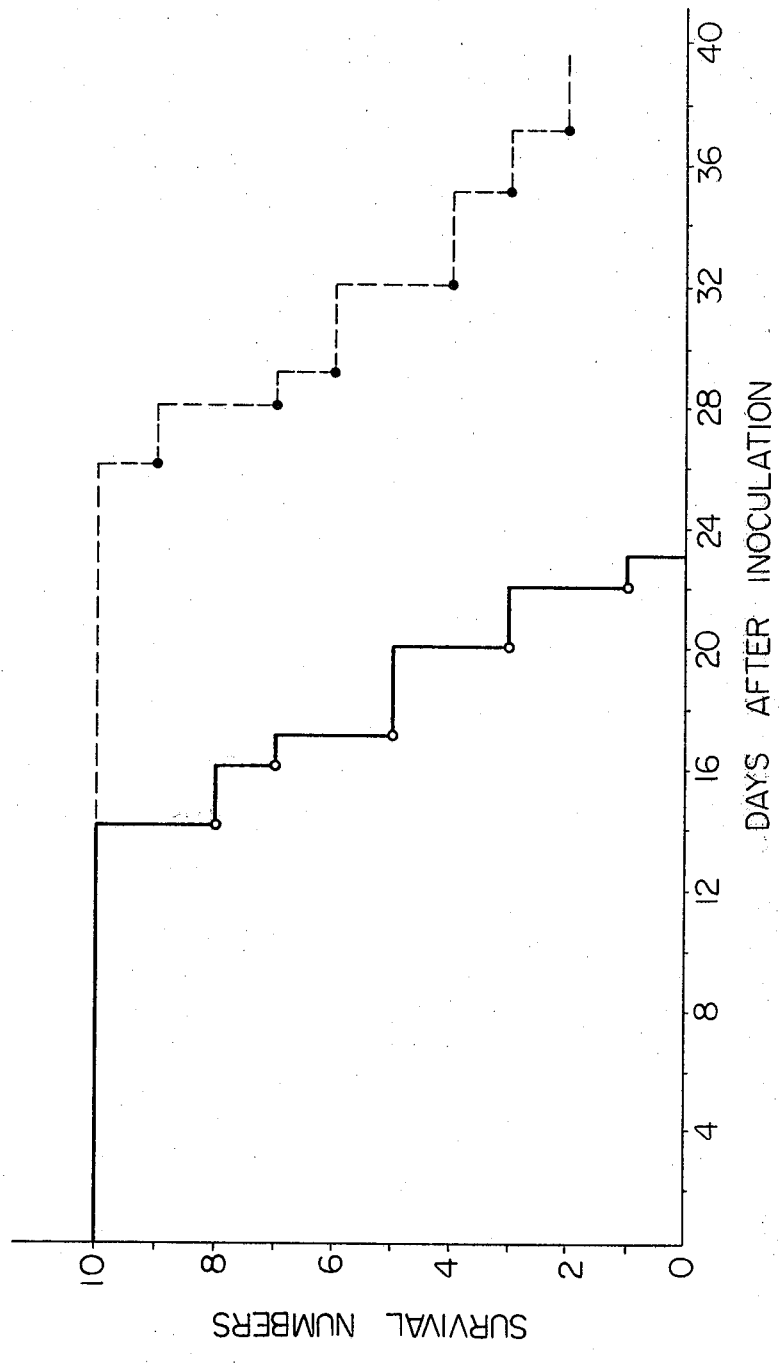
Figure 4:
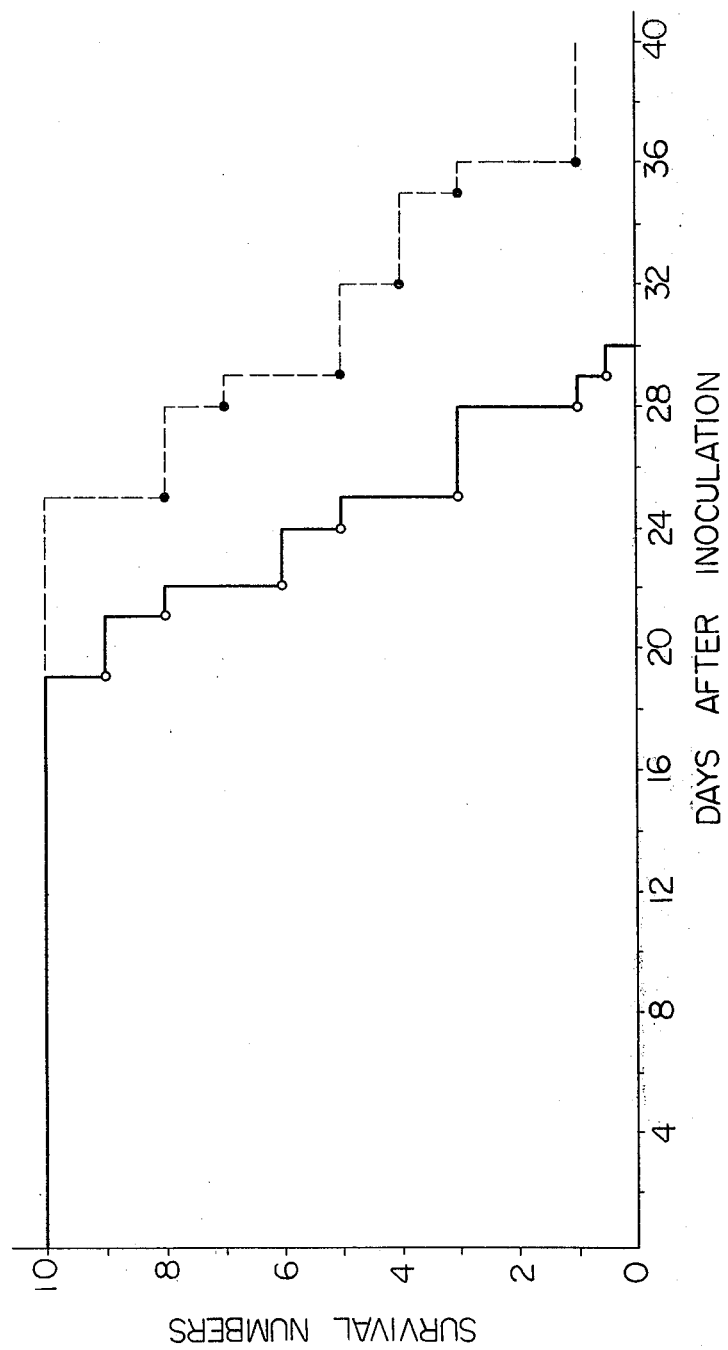

Survival numbers were observed over 40 days and the results are shown in FIGS. 2, 3 and 4. All these Figures show the effect of life-prolongation in tumor-bearing mice.

EXPERIMENTAL EXAMPLE 4

Blood was collected from a normal mouse and tumor-bearing mouse (Krebs-2). Lymphocytes were isolated by Ficol Conley's method and suspended aseptically into a culture medium for lymphocytes, RPMI-1640, to make a density of 5,000 – 10,000/cubic mm, respectively.

Each lymphocyte suspension was divided into three parts, and the nitrogen-containing carbohydrates obtained in Examples 1 and 2 were added to two of them in an amount of 10 γ/ml respectively. The rest served as a control without addition of the carbohydrate.

Each of the three suspensions was cultured at 37°C for 72 hours under 5% $CO_2$ in air. Lymphocytes were collected and stained by the method of Giemsa staining, and observed by microscope.

Microscopical observation revealed that 80 – 90 percent of the lymphocytes caused blastgenesis in the carbohydrate-added samples of a group containing lymphocytes of tumor-bearing mouse, in contrast to 10 – 20 percent in its control sample, said results in the control sample being the same as in three samples containing lymphocytes of normal mice with or without the carbohydrate, and by this phenomenon a tumor-bearing mouse could be differentiated apparently from a normal mouse.

EXAMPLE 1

Mice were inoculated with an experimental tumor Krebs-2 and on the 10th – 14th day 1,000 g of a tumor tissue was collected from the mice. The tumor tissue was washed well with chilled physiological saline solution, cut into pieces and homogenized with 5 times its volume of M/15 phosphate buffer solution, pH 6.8, for a few minutes. The homogenate was centrifuged at 12,000 $\times$ g for about 10 minutes and the supernatant was heated for 2 hours on a water bath. The resulted precipitate was removed. The supernatant was concentrated to about 1/10 its volume and twice the volume of ethanol was added to the concentrate. The resulted precipitate was collected, dissolved in 30 times its volume of M/15 phosphate buffered saline solution, and the solution was filtered through ultrafiltration membrane using DIAFLO (available from Amicon Corp.) for fractionation. The residual material on the membrane was dissolved in a small amount of distilled water and the solution was passed through an anion exchange resin column of Dowex 1 $\times$ 10 (available from Dow Chemical Co.), which had been bufferized with ammonium formate at a pH 6.0, to remove proteineous impurities. The eluate was passed through a dextran gel column of Sephadex G-75 (available from Pharmacia Fine Chemicals, Sweden) and the active substance was eluted with M/15 phosphate buffer solution, pH 6.8. The eluate was dialyzed against running water in a cellophane tube to remove inorganic salts, and the dialysate was condensed and distilled in vacuo with about 2 times its volume of ethanol to give 105 mg of a powdery product.

EXAMPLE 2

2,000 g of a tumor tissue (original hepatoma) collected from human being, was washed well with chilled physiological saline solution, cut into pieces and homogenized with 10 times its volume of M/15 phosphate buffer solution, pH 6.8, for a few minutes. The homogenate was centrifuged at 12,000 $\times$ g for about 10 minutes and the supernatant was heated for 2 hours on a water bath. The resulted precipitate was removed. The supernatant was concentrated to about 1/10 its volume and twice its volume of ethanol was added to the concentrate. The resulted precipitate was collected, dissolved in 30 times its volume of M/15 phosphate buffered saline solution, and the solution was filtered through ultrafiltration membrane using DIAFLO (available from Amicon Corp.) for fractionation. The residual material on the membrane was dissolved in a small amount of distilled water and the solution was passed through an anion exchange resin column of Dowex 1 $\times$ 10 (available from Dow Chemical Co.), which had been bufferized with 0.01M ammonium formate at a pH 6.0, to remove proteineous impurities. The eluate was passed through a dextran gel column of Sephadex G-75 (available from Pharmacia Fine Chemicals, Sweden) and the active substance was eluted with M/15 phosphate buffer solution, pH 6.8. The eluate was dialyzed against running water in a cellophane tube to remove inorganic salts, and the dialysate was condensed and distilled in vacuo with about 2 times its volume of ethanol to give 210 mg of a powdery product. The product was the same as that obtained in Example 1.

EXAMPLE 3

The embryos were removed from 14 – 18 days-pregnant mice and 50 g of embryonal liver was collected. The embryonal liver tissue was washed well with chilled physiological saline solution, cut into pieces and homogenized with 2.5 times its volume of M/15 phosphate buffer solution, pH 6.8, for a few minutes. The homogenate was centrifuged at 12,000 $\times$ g for about 10 minutes and the supernatant was heated for 2 hours on a water bath. The resulted precipitate was removed. The supernatant was concentrated to about 1/10 its volume and twice its volume of ethanol was added to the concentrate. The resulted precipitate was collected, dissolved in 30 times its volume of M/15 phosphate buffered saline solution, and the solution was filtered through ultrafiltration membrane using DIAFLO (available from Amicon Corp.) for fractionation. The residual material on the membrane was dissolved in a small amount of distilled water and the solution was passed through an anion exchange resin column of Dowex 1 $\times$ 10 (available from Dow Chemical Co.), which had been bufferized with 0.01M ammonium formate at a pH 6.0, to remove proteineous impurities. The eluate was passed through a dextran gel column of Sephadex G-75 (available from Pharmacia Fine Chemicals, Sweden) and the active substance was eluted with M/15 phosphate buffer solution, pH 6.8. The eluate was dialyzed against running water in a cellophane tube to remove inorganic salts, and the dialysate was condensed and distilled in vacuo with about 2 times its volume of ethanol to give 5 mg of a powdery product. The product was the same as those obtained in Examples 1 and 2.

Figure 5:
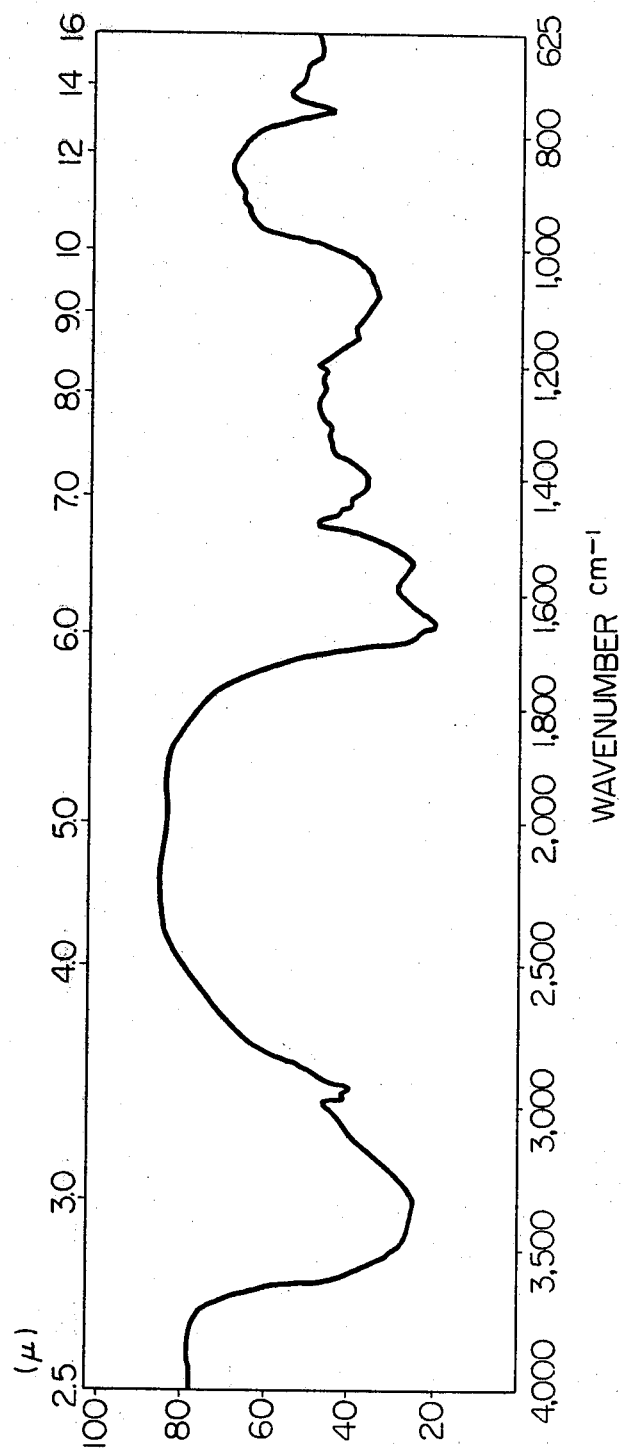
FIG. 5 shows infrared absorption spectrum of the nitrogen-containing carbohydrate (KBr disc method).

What we claim is:
1. The nitrogen-containing carbohydrate having the following physicochemical properties:
    1. Appearance:
        Colorless, powdery
    2. Solubility:
        Easily soluble in water; Hardly soluble in organic solvents such as methanol, ethanol, acetone and ether
    3. Melting point:
        230°C (decomposed)
    4. Ultraviolet absorption spectrum:
        No characteristic absorption
    5. Infrared absorption spectrum:
        The spectrum is shown in FIG. 5 (KBr disc method); Absorptions: 3400 – 3300, 1650, 1550, 1400, 1070 cm$^{-1}$
    6. Elemental analysis:
        C; 34.4%, H; 9.7%, N; 8.2%, O; 38.2%
    7. Molecular weight:
        Ranges between 10,000 and 30,000
    8. Color reaction:

| | |
|---|---|
| Elson-Morgan's reaction | Positive |
| Molish reaction | Positive |
| Anthron reaction | Positive |

-continued

| | |
|---|---|
| Diphenylamine-HCl reaction | Positive |
| Ninhydrin reaction | Negative |
| Sialic acid reaction with Ehrlich's reagent | Negative |

9. Specific rotatory power:
$[\alpha]_D^{20} = -12°$.

* * * * *